United States Patent [19]
Iwasaki

[11] Patent Number: 5,807,344
[45] Date of Patent: Sep. 15, 1998

[54] ARTERIAL BLOOD GAS SYRINGE INCLUDING FILTER MEMBER

[75] Inventor: Dean H. Iwasaki, Denver, Colo.

[73] Assignee: In-x Corporation, Lakewood, Colo.

[21] Appl. No.: 797,134

[22] Filed: Feb. 10, 1997

[51] Int. Cl.⁶ .................................................. A61M 5/00
[52] U.S. Cl. ........................ 604/190; 128/763; 128/765
[58] Field of Search .................................... 604/190, 218, 604/187; 128/760–766

[56] References Cited

U.S. PATENT DOCUMENTS

| | | | |
|---|---|---|---|
| 3,493,503 | 2/1970 | Mass | 210/59 |
| 4,061,143 | 12/1977 | Ishikawa | 128/218 N |
| 4,466,446 | 8/1984 | Baidwan et al. | 604/190 X |
| 4,525,374 | 6/1985 | Vaillancourt | 427/2 |
| 4,572,210 | 2/1986 | McKinnon | 128/765 |
| 4,660,569 | 4/1987 | Etherington | 604/190 X |
| 4,687,000 | 8/1987 | Eisenhardt et al. | 128/760 |
| 4,703,763 | 11/1987 | McAlister et al. | 128/765 |
| 4,902,421 | 2/1990 | Pascale et al. | 210/416.1 |
| 4,957,637 | 9/1990 | Cornell | 210/782 |
| 5,238,003 | 8/1993 | Baidwan et al. | 128/765 |
| 5,377,689 | 1/1995 | Mercereau | 128/763 |
| 5,494,044 | 2/1996 | Sundberg | 128/749 |

*Primary Examiner*—John D. Yasko
*Attorney, Agent, or Firm*—Sheridan Ross P.C.

[57] ABSTRACT

A syringe device for obtaining an arterial blood sample is provided. The syringe device includes a syringe barrel, a plunger assembly having a sealing plug and a filter member. The syringe device preferably includes a carrying device including an anticoagulant and a carrying device body. The carrying device body is made of a hard, non-porous material. The filter member permits the passage of air while preventing the passage of blood. The filter member has a periphery that is in contact with the inner wall of the syringe barrel so that the air does not pass along the inner wall past the filter member. Preferably, the filter member is detached from the sealing plug. During operation, a blood sample from a patient is received in a blood receiving area defined in the syringe barrel, while displaced air passes through the filter member and is substantially contained between the filter member and the sealing plug.

14 Claims, 4 Drawing Sheets

ARTERIAL BLOOD GAS SYRINGE INCLUDING FILTER MEMBER

FIELD OF THE INVENTION

The present invention relates to syringes for obtaining blood samples and, in particular, to arterial blood gas syringes that use a filter for preventing the passage of blood.

BACKGROUND OF THE INVENTION

Arterial blood gas (ABG) syringes are used to obtain arterial blood samples from a patient. The arterial blood is tested using an appropriate instrument or analyzer. The test results provide useful information about the condition of the patient and potential treatment, if appropriate. Numerous ABG syringes have been proposed or devised over decades of usages of this class of syringes. Currently known or marketed ABG syringes commonly have a plunger assembly within a barrel. It is also common practice to include a filter medium attached to a sealing plug, with the sealing plug being part of the plunger assembly. The filter medium permits air to vent or escape as blood is received from the patient, but prevents the passage of blood so that a liquid tight seal is achieved. The removal of air is important so that the analyzed blood sample essentially does not have unwanted gases that would improperly affect the analysis. It is further known to include an anticoagulant in the syringe barrel between its blood receiving end and the sealing plug. In one implementation, the anticoagulant is deposited on a soft, porous carrier body. Although available ABG syringes adequately meet general criteria and perform well in obtaining an arterial blood sample, it would be worthwhile to provide an ABG syringe that accomplishes the same functions and results of prior art syringes, together with incorporating further desirable functions and advantages.

SUMMARY OF THE INVENTION

In accordance with the present invention, an ABG syringe device is provided for obtaining a blood sample from a patient in which displaced air is essentially captured or trapped between a filter member and a sealing plug. The syringe device includes a barrel and a plunger assembly. The sealing plug is part of the plunger assembly. The filter member is adjacent, but spaced from, a front face of the sealing plug when the filter member and the sealing plug are positioned within the syringe barrel. The filter member has a periphery. When the filter member is located within the barrel, the periphery contacts the inner wall of the barrel. This contact is sufficient to prevent air from passing or escaping past the periphery at the inner wall of the barrel. Preferably, the filter member is detached from the sealing plug and the space or gap that is defined between the front face of the sealing plug and the filter member receives the displaced air that passes through the filter member, with such air being prevented by the sealing plug from further movement in a direction towards the back of the syringe.

With regard to the assembly of the parts and use of the syringe device, the filter member can be inserted into the syringe barrel separately from the sealing plug and other parts of the plunger assembly. Typically, the filter member is placed adjacent to the blood receiving end of the syringe barrel. Likewise, the sealing plug is disposed adjacent to the filter member at this end of the syringe barrel. The syringe device of the present invention can obtain a blood sample by an arterial puncture or by means of an in-line catheter. In the case of an arterial puncture in which the needle penetrates or pierces an artery, when the arterial blood is received by the needle and passes through the blood receiving end, it contacts the filter member adjacent to this end. The pressure from the arterial blood is able to cause movement of the filter member away from the blood receiving end, as well as concomitant movement of the sealing plug. Parenthetically and conversely, if a vein is inadvertently punctured, instead of an artery, the blood pressure will be insufficient to move or push back the filter member thereby indicating to the technician or operator that an artery was not punctured. As the arterial blood occupies the blood receiving area in the syringe barrel, air is displaced by the blood. The filter member allows the air to pass through it while the material composition of the filter member prevents the passage of blood through the filter member. The gap or space between the filter member and sealing plug is sufficient to receive and hold the displaced air. Upon the desired amount of blood being received to constitute the blood sample contained in the blood receiving area, the technician then discontinues obtaining further blood and follows usual procedures in connection with analyzing the blood sample.

The syringe device can also be used to obtain arterial blood from an in-line catheter connected to an artery. Essentially the same operation and procedures are involved, except no syringe needle piercing is necessary.

The syringe device is also capable of obtaining an arterial blood sample when arterial blood pressure is insufficient to force the filter member rearward or, alternatively, is not great enough to fill the pre-set blood receiving area. In such a case, the plunger assembly is pulled back to aspirate the blood sample into the syringe.

The syringe device additionally preferably includes a carrying device having an anticoagulant attached to its outer surface. The carrying device is made of a hard, plastic-like material that is non-porous. The carrying device has a "material density" that enables the carrying device to cause a "breach" through the top layer of blood (meniscus) in order to eliminate potential air bubble trapping between or around the carrying device and the filter member. Further, the surface area of the carrying device needs to be sufficient to accommodate bonding and the subsequent release of the anticoagulant from the carrying device. Because of the inherent size limitations due to its placement in the syringe barrel, the amount of its surface area is augmented by a carrying device having a surface area with a number of dimples or bumps.

Based on the foregoing summary, a number of salient aspects of the present invention are readily discernible. A syringe device is disclosed for obtaining an arterial blood sample while trapping all or substantially all of the displaced air between a filter member and a sealing plug. The filter member is, preferably, separate from the plug member and is able to move under arterial blood pressure. Movement of the filter member by virtue of the pressure of the received blood is also useful as an indicator to inform the operator that arterial blood and not venus blood is being received. The filter member has a periphery that is in sufficient contact with the inner wall of the syringe barrel to avoid air passage along the inner wall of the barrel past the filter member. The syringe of the present invention can be used in an aspirating mode to draw arterial blood into the syringe barrel, together with the anticipated normal mode of operation in which the filter member is caused to be moved back by means of arterial blood pressure. The syringe device can be used in an arterial piercing, as well as with an in-line catheter connected to an artery. The syringe device also has a carrying device with an anticoagulant that is releasable and mixable with the blood when it is received into the syringe device in order to prevent coagulation of the drawn blood.

DETAILED DESCRIPTION

Figure 1:
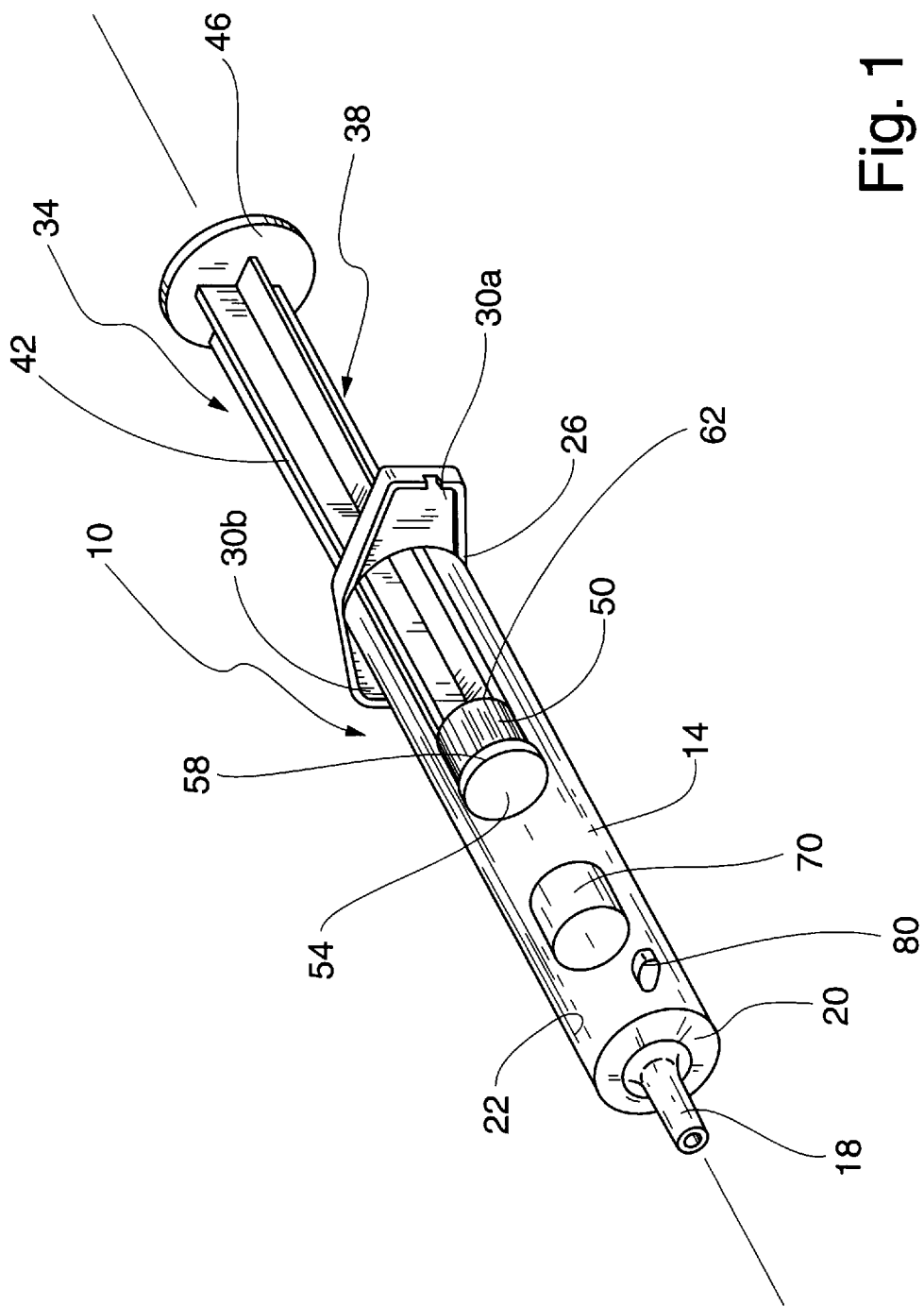
FIG. 1 is a perspective view of the syringe device of the present invention.

With reference to FIG. 1, an arterial blood gas syringe 10 is illustrated. The ABG syringe device 10 is useful in obtaining an arterial blood gas sample from a patient. Subsequently, the blood sample is analyzed by ejecting it from the syringe device 10 into an analyzer that is able to analyze the blood gases, for example, in the sample.

The syringe device 10 includes a syringe barrel 14 that is generally cylindrical in shape along its length and at a first or blood receiving end 20, has a luer 18 to which a needle can be removably attached. A blood receiving area 22 is definable adjacent to the blood receiving end 20. The blood receiving area 22 is variable, depending upon the amount of the blood sample that is received by the syringe barrel 14. A second, or open, end 26 of the syringe barrel 14 is found at an opposite end from that of the blood receiving end 20. At this open end 26, a pair of wings 30a, 30b are provided for desired gripping by the operator or technician when a blood sample is being obtained, such as when an artery is being pierced.

Figure 2:
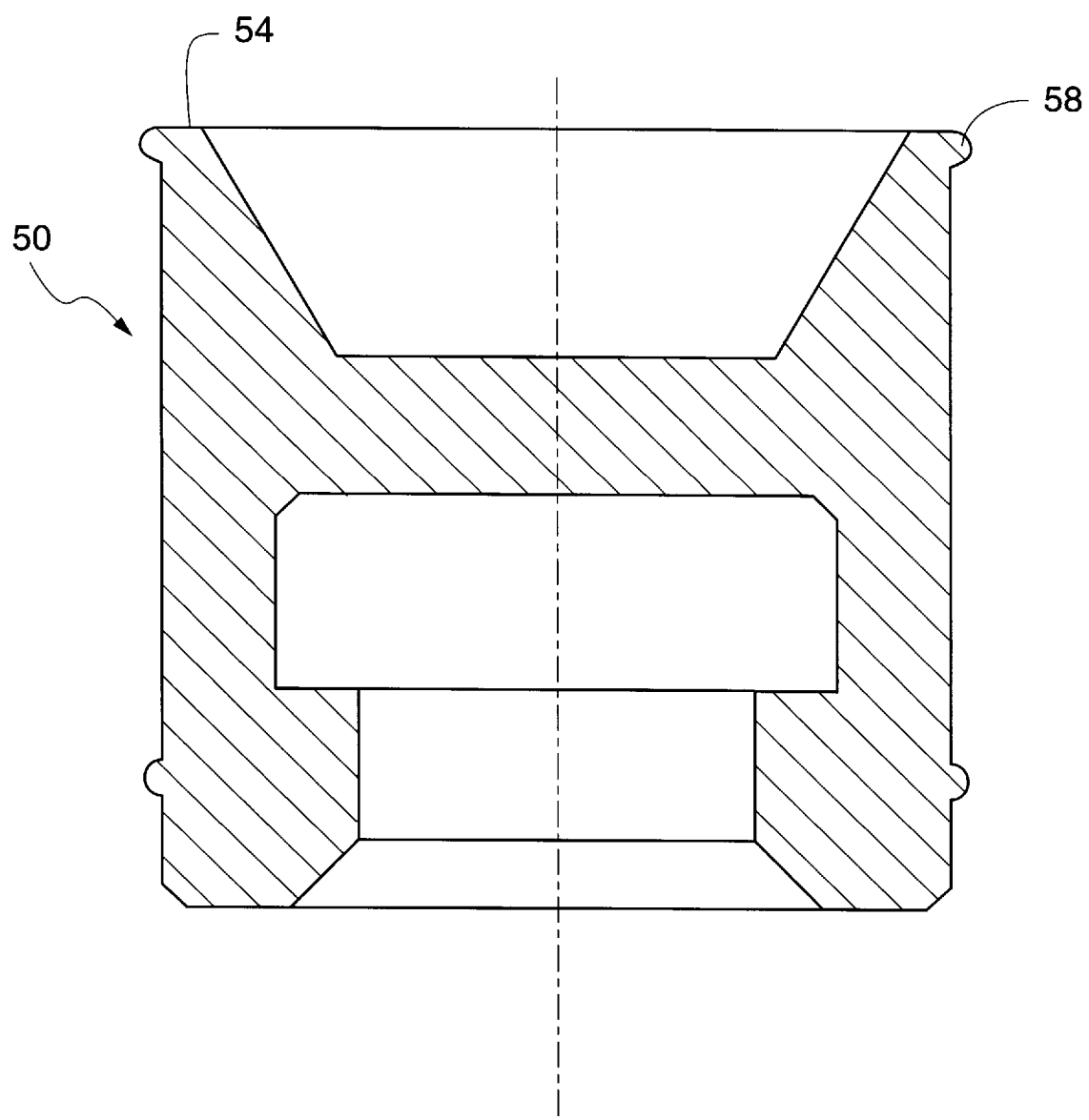
FIG. 2 is a longitudinal cross-sectional view of the plug member.

The syringe device 10 further includes a plunger assembly 34. The assembly 34 includes a plunger rod 38 having a shaft 42 that terminates at one end in a disk-shaped member 46 for beneficial grasping by the operator in connection with providing relative movement between the plunger assembly 38 and the syringe barrel 14. At the opposite end of the shaft 42, a sealing plug 50 is connected thereto. The sealing plug 50 provides a substantially fluid-tight seal when it is positioned within the syringe barrel 14. In creating this seal, the sealing plug 50 includes a front face 54 having a sealing periphery 58. The sealing periphery 58 has a width or diameter that provides desired engagement between the sealing periphery 58 and an inner wall of the syringe barrel 14. That is, with the sealing plug 50 within the syringe barrel 14, the sealing periphery 58 sufficiently contacts the inner wall of the syringe barrel 14 to provide a sealing function so that blood does not move past the sealing periphery 58. Consequently, no air from the environment is able to pass from the open end 26 of the syringe barrel 14 in a direction past the sealing plug 50. Unwanted air contamination of an obtained blood sample by air that might pass in this direction is thereby avoided. Preferably, the sealing plug 50 has a rear periphery 62, which also sealingly engages the inner wall of the syringe barrel 14. Referring to FIG. 2, the sealing plug 50 is illustrated in an enlarged size showing a cross-section thereof. As seen in FIG. 2, the sealing plug 50 has a cavity 66 for receiving the end of the shaft 42 opposite that of the disk member 46.

Figure 6:
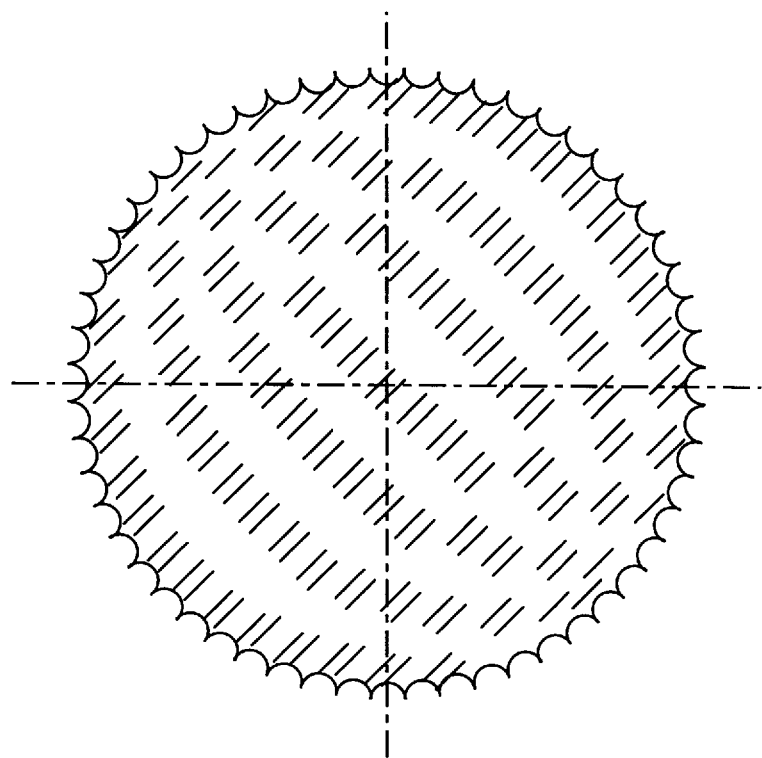
FIG. 6 is an enlarged perspective view of a carrying device on which an anticoagulant can be deposited.

The syringe device 10 also includes a filter member 70 that is disposed in the syringe barrel 14 between the blood receiving end 20 and the sealing plug 50. The filter member 70 includes a material that allows for air to pass through it, while preventing liquid, such as blood, from passing through the filter member 70. The filter member 70 has a diameter or width that contacts the inner wall of the syringe barrel 14 and sufficiently contacts the inner wall such that blood does not pass between the inner wall and the periphery of the filter member 70. Preferably, the filter member 70 is a separate item from the sealing plug 50 so that it is detached therefrom, with a space or gap 72 being defined between the upper face 54 of the sealing plug 50 and a lower face 74 of the filter member 70. Other configurations may be feasible so long as there is some gap or space into which air passes from the filter member 70 towards the front face 54. As diagrammatically illustrated in FIG. 1, the syringe 10 preferably also includes a carrying device having an anticoagulant, such as heparin, provided thereon. To overcome free ionized calcium binding, yet provide adequate sample anticoagulation, the approximate heparin unit amount per 2.5 cc syringe is 8 units. After the manufacturing process, during which the carrying device 80 is provided with the anticoagulant, the carrying device is located in the defined blood receiving area 22 of the syringe 10 for use in inhibiting coagulation of the blood sample. The body 84 of the carrying device 80 has certain structural requirements or properties. The carrying device body 84 has a "material density" that readily breaks or breaches the meniscus or top layer of blood which first enters the syringe 10 during the obtaining of a blood sample. This top layer maintains some degree of surface tension. The material density of the carrying device body 84 is of a magnitude to eliminate potential air bubble trapping between or around the carrying device 80 and the filter member 70. Adequate material density also insures proper movement of the carrying device 80 through the blood sample to insure proper anticoagulant and blood mixing. The material density of the carrying device body 84 should be at least greater than one gram/cc since less than that means that the carrying device 80 could float due to the surface tension of the blood. The carrying device body 80 also meets a minimum or threshold surface area. Due to the physical size constraints placed on the carrying device 80, in view of its placement in the syringe device 10, particular configurations of a carrying device body 84 must be such to meet or accomplish the threshold surface area. With reference to FIG. 6, in one embodiment, the carrying device body 84 has a surface that has a number of dimples or bumps 88. As can be appreciated, the number and size of such bumps can vary provided that the threshold surface area is satisfied. For example, a somewhat roughened exterior surface of the carrying device body 84, in contrast to a smooth surface area, could be employed to meet the surface area requirement. The surface area of the carrying device body 84 should be at least 0.1 sq. in. and preferably greater than about 0.15 sq. in. Relatedly, the carrying device body 84 has other properties including being non-porous, such as being made from a hard, plastic-like material, such as polystyrene, polypropylene and acrylic. Due to the non-porosity, when blood is received into the syringe device 10 having the carrying device 80, blood is maintained at the surface of the carrying device body 84 and does not penetrate the surface. Furthermore, the weight of the carrying device 80 including the combination of the anticoagulant and the carrying device body 84 decreases when contacted with blood since the anticoagulant mixes with the blood and no blood penetrates the carrying device body 84, which would cause its weight to increase.

Figure 3:
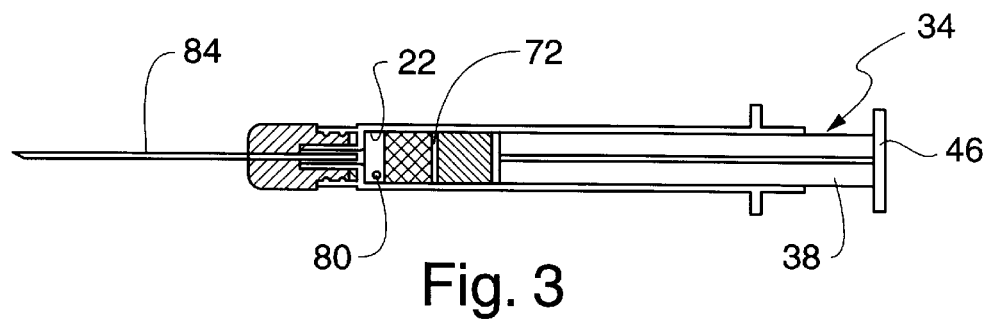
FIG. 3 is a longitudinal section illustrating positioning of the filter member and plunger assembly prior to receipt of arterial blood.
Figure 4:
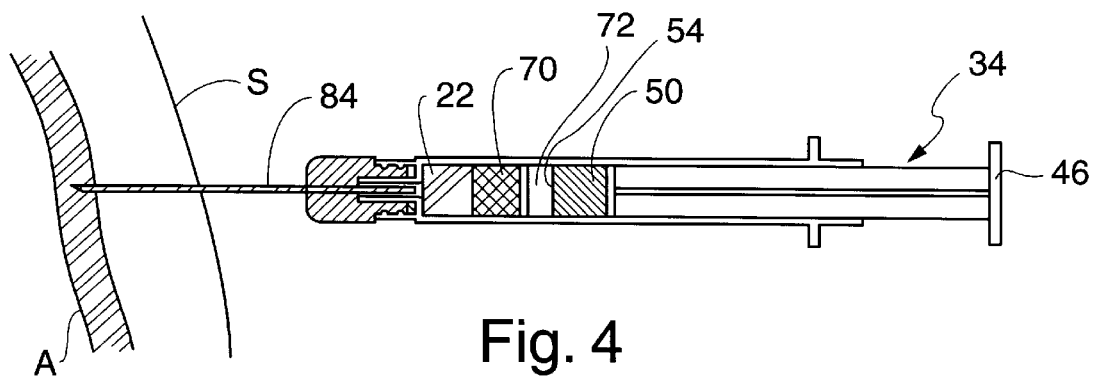
FIG. 4 illustrates obtaining an arterial blood sample by means of an arterial piercing including the blood contacting the filter member.
Figure 5:
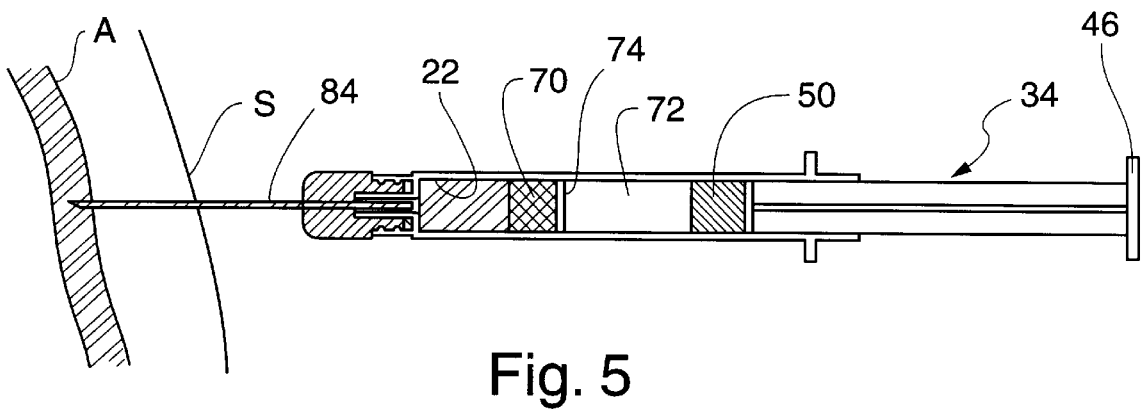
FIG. 5 illustrates a further step in connection with obtaining an arterial blood sample showing further movement of the filter member.

With reference to FIGS. 3–5, a further description will be directed to the use and operation of the syringe device 10. As illustrated in FIG. 3, it is preferable that the syringe device be packaged or assembled whereby the filter member 70 is adjacent to or abutted up against the blood receiving end 20, with the anti-coagulant carrier 80 being in place forward of the front face of the filter member 70. As can be seen, the sealing plug 50 of the plunger assembly 34 is located adjacent to the back face 74 of the filter member 70. Even though the filter member 70 is detached from the sealing plug 50, movement of the rod 38 inwardly relative to the syringe barrel 14 can lead to engagement with the filter member 70 and movement thereof with the plunger assembly 34. In accordance with this positioning, the blood receiving area 22 that the blood sample will occupy will be created using arterial blood pressure. This is schematically illustrated in FIG. 4, which shows the syringe needle 94 penetrating the skin surface S and then piercing the artery A. After piercing, the open end of the syringe needle 84 receives, under pressure, the arterial blood, which is carried by the syringe needle to the blood receiving end 20. As conveyed by FIG. 4, some of the desired blood sample has already filled a part of the eventual blood receiving space 22. Usually, the arterial blood pressure is sufficient to move the filter member 70 in a direction away from the blood receiving end 20, as the blood contacts the front face of the filter member 70. As the blood is received within the hollow syringe needle 84, any air contained therein, as well as air that might be present adjacent to the blood receiving end 20 of the syringe barrel 14 is caused to be displaced by the volume of blood that is received. Received blood is also mixing with the anticoagulant, which is released from the carrying device body 84. The material density of the carrying device body 84 insures proper mixing of the anticoagulant and blood, as well as overcoming the meniscus of the blood that might be present and thereby avoid the trapping of unwanted air. Ultimately, the air is displaced through the filter member 70 and is contained in the gap 72 between the front face 54 of the sealing plug and the rear face 74 of the filter member 70. Additionally, the pressure developed inside the syringe barrel due to the arterial blood being received, as well as some pressure created by the air in the gap between the filter member 70 and the sealing plug 50, is able to cause movement of the plunger assembly 34 in a direction towards the open end 26 of the syringe barrel 14.

As the arterial blood continues to be received by the syringe barrel 14, eventually the operator observes that a desired volume of blood sample has been obtained. For example, in FIG. 5, the blood receiving area 22 for this blood sample is now complete, and the operator can then remove the syringe needle 84 from the artery A. FIG. 5 also represents the situation where the sealing plug 50 has separated itself from the filter member 70 by an even greater distance than that illustrated in FIG. 4 and an even greater distance than that illustrated in FIG. 3. As can be appreciated, it is possible that such a relative distancing may not and/or need not occur. After the desired volume of blood sample has been obtained, as is well-known, the operator can take appropriate steps in connection with preparing the blood sample for analysis.

The syringe device 10 is also useful in an in-line catheter embodiment. In accordance with this arrangement, a catheter is already positioned relative to a patient's artery to permit the syringe device, without syringe needle, to be attached to the catheter. In such a case, the luer 18 is joined to the catheter. Upon doing so, the syringe device 10 functions or is operable in the same way as the previously described application in which the syringe needle pierces the artery A. That is, in a typical situation, the filter member 70 is located adjacent to the blood receiving end 20 of the syringe barrel 14, and arterial pressure causes desired movement of the filter member 70 and the sealing plug 50 without blood leakage past the filter member 70. Once the desired volume of blood sample is obtained, the syringe device 10 can be removed from the in-line catheter.

It should also be understood that the syringe device 10 can be used in a pre-set mode. In accordance with this configuration, the filter member 70 and the sealing plug 50 are located at desired positions in the syringe barrel 14. More specifically, the filter member 70 is located by the operator or during assembly at a desired position along the length of the syringe barrel 14 and remains in that position to define the ultimate blood receiving area 22. In such a case, as blood is received into the syringe barrel 14, air is displaced through the filter member 70. Eventually, the arterial blood occupies all of the blood receiving area 22 that was pre-set. When this occurs, the operator discontinues the obtaining of blood from the patient.

It should also be appreciated that the syringe device 10 can be used in aspirating or drawing blood into the syringe barrel 14. This is accomplished by creating a negative pressure by the pulling or drawing back of the plunger assembly 34. This aspiration technique may be appropriate in situations where the arterial blood pressure is insufficient to cause blood to fully occupy the desired blood receiving area 22.

With regard to the embodiment in which the filter member 70 is located at or adjacent to the blood receiving end 20 and it is intended that the arterial blood pressure move the filter member 70, lack of movement due to insufficient pressure can be an indicator that the syringe needle 14 has pierced a vein, instead of an artery. In such a case, the operator or technician is provided with information that a desired arterial blood vessel was not pierced.

It should be further appreciated that the diameter or width of the filter member 70 has sufficient contact to result in a tight fit with the inner wall of the syringe barrel 14. That is, the filter member 70 is disposed in the syringe barrel 14 to provide the necessary sealing function, while still permitting easy movement thereof. This engagement avoids blood leakage, while the filter member 70 can be readily moved towards a desired position in the syringe barrel 14 in a direction towards the blood receiving end 20 by means of pushing on the rear face 74 of the filter member 70 by the front face 54 of the sealing plug 50. It is also noted that, even though the filter member 70 and the sealing plug 50 are illustrated and described as being separated and detached from each other, it is possible to design these two elements so that they are attached while still providing a gap or space for displaced air.

The foregoing discussion has been presented for purposes of illustration and description. Further, the description does not intend to limit the invention to the form disclosed herein. Variation and modification commensurate with the above teachings, within the skill and knowledge of the relevant art, are within the scope of the present invention. The embodiments described hereinabove are further intended to explain the best modes presently known of practicing the invention and to enable others skilled in the art to utilize the invention as presented, or in other embodiments, and with the various modifications required by their particular applications or uses of the invention. It is intended that the appended claims be construed to include alternative embodiments to the extent permitted by the prior art.

What is claimed is:

1. A syringe device for obtaining a blood sample, comprising:
   a barrel having an inner wall, a blood receiving end into which blood is received, a remote end opposite said blood receiving end and a blood receiving area that contains the blood sample;
   a movable rod positioned within said barrel;
   a sealing plug having a front face and connected to said rod; and
   a filter member having a body and a periphery located outwardly of said body with said filter member being spaced from said sealing plug, said filter member for permitting the passage of air, with air being passed from said blood receiving area through said filter member as blood occupies said blood receiving area and with substantially all of the air being held between said front face of said sealing plug and said filter member during receipt of the blood sample, wherein said filter member periphery is in contact with said inner wall of said barrel and said filter member periphery allows air from said blood receiving area to pass therethrough at said inner wall, said filter member periphery being of the same material as portions of said filter member body that permit air to pass and said sealing plug being of a different material than said material of said filter member periphery.

2. A syringe device, as claimed in claim 1, wherein:
   said sealing plug by itself substantially prevents the passage of air in a direction from said remote end to said blood receiving area.

3. A syringe device, as claimed in claim 1, wherein:
   said filter member is positioned at said blood receiving end of said barrel and is moved under the force of the blood sample occupying said blood receiving area.

4. A syringe device, as claimed in claim 1, wherein:
   said filter member is detached from said sealing plug and said sealing plug is the only sealing plug in said barrel.

5. A syringe device for obtaining a blood sample, comprising:
   a barrel having an inner wall, a blood receiving end into which blood is received, a remote end opposite said blood receiving end and a blood receiving area that contains the blood sample;
   a movable rod positioned within said barrel;
   a sealing plug having a front face and connected to said rod; and
   a filter member adjacent to but with a space defined between said filter member and said sealing plug, said filter member for permitting the passage of air, wherein air is passed from said blood receiving area through said filter member as blood occupies said blood receiving area and with substantially all the air being held between said front face of said sealing plug and said filter member during receipt of the blood sample;
   a carrying device contained in said barrel including a carrying device body and an anticoagulant attached thereto and with said carrying device having a weight that decreases when contacted by blood that occupies said blood receiving space.

6. A syringe device for obtaining a blood sample, comprising:
   a barrel having an inner wall, a blood receiving end into which blood is received, a remote end opposite said blood receiving end and a blood receiving area that contains the blood sample;
   a movable rod positioned within said barrel;
   a sealing plug having a front face and connected to said rod; and
   a filter member adjacent to but with a space defined between said filter member and said sealing plug, said filter member for permitting the passage of air, wherein air is passed from said blood receiving area through said filter member as blood occupies said blood receiving area and with substantially all the air being held between said front face of said sealing plug and said filter member during receipt of the blood sample;
   a carrying device contained in said barrel including a carrying device body and an anticoagulant, said carrying device body being non-porous and having an outer surface and with the blood occupying said blood receiving area failing to penetrate said outer surface.

7. A syringe device for obtaining a blood sample, comprising:
   a barrel having an inner wall, a blood receiving end into which blood is received, a remote end opposite said blood receiving end and a blood receiving area that contains the blood sample;
   a movable rod positioned within said barrel;
   a sealing plug having a front face and connected to said rod; and
   a filter member adjacent to but with a space defined between said filter member and said sealing plug, said filter member for permitting the passage of air, wherein air is passed from said blood receiving area through said filter member as blood occupies said blood receiving area and with substantially all of the air being held between said front face of said sealing plug and said filter member during receipt of the blood sample;
   a carrying device contained in said barrel including a carrying device body and an anticoagulant attached thereto, said carrying device having a material density greater than one gram/cc and a surface area of at least 0.1 sq. in.

8. A method for obtaining a blood sample, comprising:
   providing a syringe device that includes a barrel having an inner wall, a blood receiving end and a remote end and a filter member for permitting the passage of air, with said filter member having a periphery;
   positioning said filter member adjacent to said blood receiving end of said barrel and engaging said inner wall of said barrel with said periphery of said filter member that permits air to pass along said periphery;;
   receiving blood through said blood receiving end of said barrel including moving said filter member along said barrel in a direction away from said blood receiving end using pressure of blood against said filter member; and
   passing air through said filter member including said periphery thereof as blood occupies a blood receiving area defined between said blood receiving end and said filter member.

9. A method, as claimed in claim 8, wherein:
   said providing step includes locating a plunger assembly adjacent to but separated from said filter member.

10. A method, as claimed in claim 9, wherein:

said providing step includes locating a front face of a sealing plug of a plunger assembly adjacent to said filter member but separated from said filter member and in which said sealing plug is the only sealing plug in said barrel.

11. A method, as claimed in claim 9, wherein:

said providing step includes placing said filter member in said syringe barrel at a different time from said plunger assembly.

12. A method, as claimed in claim 10, wherein:

said passing step includes capturing air between said filter member and said sealing plug.

13. A syringe device for obtaining a blood sample, comprising:

a barrel having an inner wall, a blood receiving end into which blood is received, a remote end opposite said blood receiving end and a blood receiving area that contains the blood sample;

a filter member disposed within said barrel, said filter member permitting the passage of air; and a carrying device including a carrying device body and an anticoagulant, said carrying device body having an outer surface and said carrying device body being impervious to blood wherein blood in contact with said carrying device body does not penetrate said outer surface thereof, said carrying device body having a material density greater than one gram/cc and a surface area of at least 0.1 sq. in., said carrying device having a weight and in which said weight decreases when said carrying device contacts blood occupying said blood receiving area.

14. A method for obtaining a blood sample, comprising:

providing a syringe device that includes a barrel having an inner wall, a blood receiving end and a remote end, a plunger assembly including a rod and a sealing plug attached thereto and a filter member having periphery for permitting the passage of air from said blood receiving end and with said sealing plug and at least portions of said rod disposed within barrel;

receiving blood through said blood receiving end of said barrel;

passing air through said filter member including said periphery thereof as blood occupies a blood receiving area defined between said blood receiving end and said filter member; and keeping said air that passes through said filter member in a space defined between said filter member and said sealing plug using a seal provided by said sealing plug during said receiving, wherein said air is held between said filter member and said sealing plug when said rod is pulled in a direction toward said remote end and also when said rod is not being pulled in a direction toward said remote end.

* * * * *